United States Patent [19]
Weigl et al.

[11] Patent Number: 6,159,739
[45] Date of Patent: Dec. 12, 2000

[54] DEVICE AND METHOD FOR 3-DIMENSIONAL ALIGNMENT OF PARTICLES IN MICROFABRICATED FLOW CHANNELS

[75] Inventors: Bernhard Weigl; Paul Yager, both of Seattle, Wash.; James P. Brody, Pasadena, Calif.

[73] Assignee: University of Washington, Seattle, Wash.

[21] Appl. No.: 08/823,747

[22] Filed: Mar. 26, 1997

[51] Int. Cl.[7] .................................................. G01N 35/08
[52] U.S. Cl. .............................. 436/52; 436/53; 436/165; 436/172; 422/81; 422/82; 422/82.05; 422/82.08; 356/246
[58] Field of Search .................................. 436/52, 53, 63, 436/164, 165, 172; 422/81, 82, 82.05, 82.08, 82.09; 356/246

[56] References Cited

U.S. PATENT DOCUMENTS

| | | | |
|---|---|---|---|
| 3,873,204 | 3/1975 | Friedman et al. | 356/39 |
| 4,056,324 | 11/1977 | Göhde | 356/246 |
| 4,894,146 | 1/1990 | Giddings | 209/12 |
| 4,908,112 | 3/1990 | Pace | 204/299 R |
| 4,983,038 | 1/1991 | Ohki et al. | 356/246 |
| 5,007,732 | 4/1991 | Ohki et al. | 356/73 |
| 5,039,426 | 8/1991 | Giddings | 210/695 |
| 5,079,959 | 1/1992 | Miyake et al. | 73/864.85 |
| 5,159,403 | 10/1992 | Kosaka | 356/243 |

(List continued on next page.)

FOREIGN PATENT DOCUMENTS

| | | |
|---|---|---|
| 0 288 029 A2 | 4/1988 | European Pat. Off. . |
| 0 294 701 | 9/1992 | European Pat. Off. . |
| 25 21 236 A1 | 11/1976 | Germany . |
| WO 97/00442 | 1/1997 | WIPO . |

OTHER PUBLICATIONS

Chmelik, Josef, "Isoelectric focusing field–flow fractionation" *Journal of Chromatography* 545, No. 2 (1991).

Eisert, W.G. et al. (1975), "Simple flow microphotometer for rapid cell population analysis," Rev. Sci. Instrum. 46(8): 1021–1024.

Sobek et al. (1993), "A Microfabricated Flow Chamber for Optical Measurements in Fluids," in Proc. of the IEEE Micro Electro Mechanical Systems Workshop, Fort Lauderdale, Florida, Feb. 1993, pp. 219–224.

(List continued on next page.)

*Primary Examiner*—Maureen M. Wallenhorst
*Attorney, Agent, or Firm*—Greenlee, Winner and Sullivan, P.C.

[57] ABSTRACT

The present invention provides a sheath flow module made from a first plate of material having formed therein a laminar fluid flow channel; at least two inlets, each inlet joining the laminar flow channel at a junction, the first inlet junction being wider than the second inlet junction, and an outlet from the flow channel. A second plate, e.g. a transparent cover plate, seals the module and allows for optical measurements. A first inlet allows for introduction of a first fluid into the flow channel. The first fluid is the sheath fluid. A second inlet allows for introduction of a second fluid into the sheath fluid while it is flowing through the flow channel. The second fluid is the center fluid. Because the second inlet junction is narrower than the first inlet junction, the center fluid becomes surrounded on both sides by the sheath fluid. After all fluids have been introduced and sheath flow has been achieved, the depth of the flow channel can be decreased, leading to vertical hydrodynamic focusing. Optionally, the width of the flow channel can be decreased, leading to horizontal hydrodynamic focusing. The decrease in depth and width can be gradual or abrupt. The device of the present invention can function in two modes, the sheath flow mode and the particle injector mode, depending on the relative densities of the sheath fluid, the center fluid, and any particles in either fluid.

48 Claims, 12 Drawing Sheets

U.S. PATENT DOCUMENTS

| | | | |
|---|---|---|---|
| 5,240,618 | 8/1993 | Caldwell et al. | 210/748 |
| 5,674,743 | 10/1997 | Ulmer | 435/287.2 |
| 5,716,852 | 2/1998 | Yager et al. | 436/172 |
| 5,726,751 | 3/1998 | Altendorf et al. | 356/246 |
| 5,747,349 | 5/1998 | van den Engh et al. | 436/172 |
| 5,932,100 | 8/1999 | Yager et al. | 210/634 |
| 5,948,684 | 9/1999 | Weigl et al. | 436/52 |
| 5,972,710 | 10/1999 | Weigl et al. | 436/34 |

OTHER PUBLICATIONS

Gravesen, P. et al. (1993), "Microfluidics — a review," J. Micromech. Microeng 3:168–182.

Kikuchi, Y. et al. (1992), "Optically Accessible Microchannels Formed in a Single–Crystal Silicon Substrate for Studies of Blood Rheology," Microvascular Res. 44:226–240.

Miyake, R. et al. (1991), "A Development of Micro Sheath Flow Chamber," in Proceedings of the IEEE Micro Electro Mechanical Systems Workshop, Nara, Japan, Jan. 1991, pp. 265–270.

Verpoorte, E. et al. (1993), "A silicon flow cell for optical detection in miniaturized total chemical analysis systems," Sensors and Actuators B 6:66–70.

Wilding, P. et al. (1994), "Manipulation and Flow of Biological Fluids in Straight Channels Micromachined in Silicon," Clin. Chem. 40(1):43–47.

Sobek, D. et al. (1994), "Microfabricated Fused Silica Flow Chambers for Flow Cytometry," Solid State Sensor and Actuators Workshop, Hilton Head, South Carolina, Jun. 1994, 4 pp.

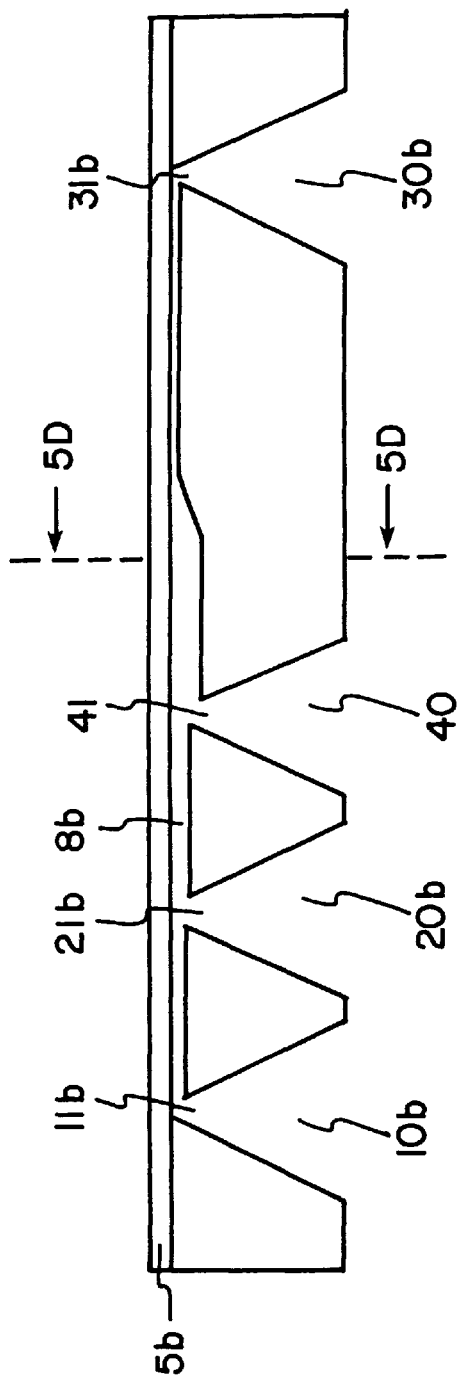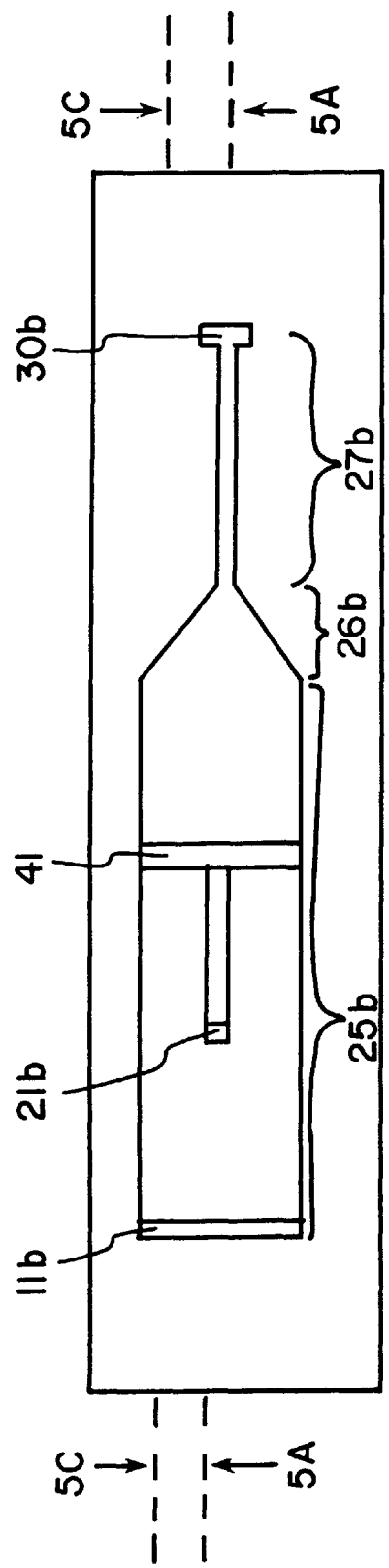

DEVICE AND METHOD FOR 3-DIMENSIONAL ALIGNMENT OF PARTICLES IN MICROFABRICATED FLOW CHANNELS

This invention was made with government support. The government has certain rights therein.

FIELD OF INVENTION

This invention relates generally to an apparatus and methods for achieving sheath flow using a microfabricated flow channel. The invention is useful, for example, for injecting small particles into a sheath stream, for achieving sheath flow in a flow cytometer and in creating hydrodynamic focusing.

BACKGROUND OF THE INVENTION

Flow cytometry is a sensitive and versatile probe of the optical characteristics of microscopic particles, with widespread applications including hematology, immunology, genetics, food science, pharmacology, microbiology, parasitology, and oncology. Optical flow cytometers use light scattering and fluorescence to determine physical and chemical properties of the particles. For measurement, particles are arranged in single file, typically by hydrodynamic focusing within a sheath fluid, and interrogated by a light beam propagating orthogonal to the flow axis. Flow cytometers often use two concentric fluids to carry particles through the measurement zone, where optical measurement occurs. The use of two concentric fluids facilitates the passage of the particles through the measurement zone in a single file fashion, and helps avoid clogging of the flow channel. Hydrodynamic focusing is a phenomenon that leads to a single file flow of particles as a result of the very small dimensions of the flow channel. A sample is injected into a flowing sheath fluid; the dimensions of the flow channel become more narrow, causing the dimensions of the stream of sample to become more narrow also. FIG. 1 is a cross section of flow in an art-known sheath flow accomplished by injecting, via a needle or other concentric opening, a center fluid (41) containing a sample with particles (42) into a sheath fluid (40), surrounded by air. Hydrodynamic focusing requires laminar flow of the fluids; any turbulence would cause mixing of the concentric fluids. The optical properties of the particles are measured in the measurement zone. Scattered light and fluorescence are measured by two or more photodetectors positioned around the illuminated portion of the flow stream. A first photodetector can be positioned to collect small angle scattering. A second photodetector is often positioned at about 90° to the forward scattering direction to collect large angle scattering and fluorescence.

Existing commercial cytometers are large and complicated instruments requiring skilled operators. To increase the accessibility of flow cytometry, compact cytometers are desired.

The flow behavior of liquids at the microscopic level is significantly different from the flow behavior of liquids at the macroscopic level. In microstructures, i.e. microfabricated fluidic devices, practically all flow is laminar, as a result of the extremely small channel diameters. Laminar flow allows two or more fluids to flow parallel to each other without turbulence-induced mixing. However, because the channel diameters are very small, diffusion is significant. Since diffusion occurs in all directions, a component of one layer may diffuse to another layer, perpendicular to the direction of flow.

Sheath flow is a particular type of laminar flow in which one layer is surrounded by another layer on more than one side. Concentric layers of fluids, that is, where one layer is completely surrounded on all sides by another layer, is one example of sheath flow. Sheath flow is useful because it positions particles with respect to illuminating light, e.g., a laser beam, and it prevents particles in the center fluid, which is surrounded by the sheath fluid, from touching the sides of the flow channel and thereby prevents clogging of the channel. Sheath flow allows for faster flow velocities and higher through-put of sample material. Faster flow velocity is possible without shredding cells in the center fluid because the sheath fluid protects the cells from shear forces at the walls of the flow channel. Sheath flow is useful in many applications, including but not limited to, any application in which it is preferable to protect particles by a layer of fluid, for example in applications wherein it is necessary to protect particles from air. Other applications include flow cytometry and combustion processes wherein an inner core layer burns at a different temperature from that of an outer layer. In the latter application, the sheath flow module of this invention can be used to create a flame of two or more combustible fluids with the outer sheath fluid burning, for example, at a higher temperature than the inner core fluid. In this case, the outer sheath fluid can be used to heat the inner core fluid. Of course, the temperatures of the fluids can be reversed, i.e., the outer sheath fluid can be one which burns at a lower temperature than the inner core fluid. Control of flame shape or color is possible using the sheath flow module of this invention.

In a microfabricated flow channel, a challenge is to focus light into the channel and to collect near forward scattered and high angled scattered light out of the channel. A few microfabricated flow cytometer flow channels have been reported. Miyake et al. [Proceedings of the IEEE Micro Electro Mechanical Systems Workshop, pp. 265–270, Nara, Japan, January 1991] describes a micromachined sheath flow channel made of five stacked plates. Three metal plates are used to create a flow having a sample core within a sheath, and glass plates on the top and bottom of the stack provide optical access to the flow channel for illumination through the top and forward scattered light collection through the bottom. The top and bottom plates provide a sheath fluid inlet. The middle plate provides for the sample inlet in the center, with the sheath fluid inlets on both sides. It appears that 90° scattering cannot be collected. Sobek et al. [Proceedings of the IEEE Micro Electro Mechanical Systems Workshop, pp. 219–224, Fort Lauderdale, Fla., February 1993] describes a four-layer silicon microfabricated hexagonal sheath flow channel. The channel is formed between two of the silicon wafers. Integrated optical waveguides intersecting the channel are used to couple laser light into the channel and out of the channel in the forward direction. At this intersection, the top and bottom walls of the channel are silicon nitride/silicon dioxide windows for 90° light collection. Each window is fabricated by growing an oxide layer on a silicon wafer, bonding the oxide layer to a second silicon wafer, etching away the silicon on both sides of the oxide at the window region and depositing a nitride layer. Sheath flow with a sample in the center of the sheath stream is accomplished by injecting sample via a hypodermic needle into the center of the stream of sheath fluid. Sobek et al. [Proceedings of the Solid-State Sensors and Actuators Workshop, Hilton Head, S.C., June 1994] describes a sheath flow channel fabricated between two fused silica wafers. To couple light into the channel and out in the forward direction, optical fibers are sandwiched between the wafers orthogonal to the flow axis. Fluorescence is collected through the upper transparent wafer. Again, sheath flow is accomplished by injection of the sample via a hypodermic needle into the center of the sheath stream.

U.S. Pat. No. 5,726,751, "Silicon Microchannel Optical Flow Cytometer," issued Mar. 10, 1998, which is incorporated by reference herein in its entirety, discloses a flow cytometer comprising a v-groove flow channel formed by micromachining a silicon wafer. This reference describes a flow cytometer made of two components: a flow cytometer optical head and a disposable flow module. The flow module of this reference exploits the fact that anisotropic etching of single crystalline silicon wafers provides access to reflective surfaces with precisely etched angles relative to the surface of the wafer. The facets are used for reflecting, as opposed to transmitting, an illuminating laser beam. This reference suggests the use of a sheath flow in a v-groove but does not teach a novel method or apparatus for achieving sheath flow.

SUMMARY OF THE INVENTION

The present invention provides a sheath flow module made from a first plate, which is a single piece of material, and a second plate, which is preferably a transparent cover plate. This module allows for sheath flow creation and optical measurements of a sample of interest. The sheath flow module of the present invention can be employed to achieve sheath flow on a microscale for use in flow cytometry. An object of the present invention is to provide a flow module for reproducibly focusing particles into the measurement zone of a flow cytometer. Another object of the invention is to prevent particles from touching the walls/sides and bottom and top of the flow channel.

The present invention provides a sheath flow module made from a first plate of material having formed therein a laminar fluid flow channel; at least two inlets, each inlet joining the laminar flow channel at a junction, the first inlet junction being wider than the second inlet junction, and an outlet from the flow channel. A second plate, e.g. a transparent cover plate, seals the module and allows for optical measurements.

The present invention provides the creation of sheath flow from a single plate with formed features, covered by a second plate. The second plate can either be a flat cover plate, preferably transparent, or it can have a channel and/or inlets and/or an outlet formed therein. A transparent cover plate allows for optical measurements by reflection, in cases where the first plate is a reflective material, e.g. silicon. In cases where the first and second plates are both transparent, optical measurements can be performed by transmission. There is no need to fabricate and align multiple plates or use a syringe needle for injection.

A first inlet allows for introduction of a first fluid into the flow channel. The first fluid is the sheath fluid. A second inlet allows for introduction of a second fluid into the sheath fluid while it is flowing through the flow channel. The second fluid is the center fluid. Because the second inlet junction is narrower than the first inlet junction, the center fluid becomes surrounded on both sides by the sheath fluid.

The device of the present invention can function in two modes, the sheath flow mode and the particle injector mode, depending on the relative densities of the sheath fluid, the center fluid, and any particles in either fluid.

The first mode, termed the sheath flow mode, is for fluids and particles of approximately equal densities, and creates sheath flow by introducing a center fluid, via a narrow inlet junction, into an established sheath fluid. Unlike the previously known devices which create sheath flow (e.g. Miyake et al.), the present invention does not need sheath inlets on each side of the flow channel. Optionally, to get sheath fluid above and below the center fluid so that the center fluid is entirely surrounded by sheath fluid, a third inlet can be provided for introduction of sheath fluid downstream of the center fluid (second) inlet. The sheath flow module may be oriented in any way, e.g., horizontally, vertically, or tilted (with respect to the long axis of the flow channel).

In this mode the inlets may be on the bottom or top of the flow channel. This results in sheath fluid on two sides and either the top or the bottom, respectively. If the module is oriented with the inlets on the bottom of the flow channel, then upon introduction of the center fluid, sheath flow is accomplished with the center fluid surrounded by the sheath fluid on the top and on the sides. Alternatively, if the module is oriented with the inlets on the top of the flow channel, then upon introduction of the center fluid, sheath flow is accomplished with the center fluid surrounded by the sheath fluid on the bottom and on the sides.

To surround the center fluid on all sides, the sheath flow module of the present invention may further comprise additional inlets, for instance, a third inlet, downstream of the second inlet. The third inlet may be used to introduce any desired fluid. For example, a third inlet may be included to introduce a second layer of sheath fluid so that the center fluid is surrounded on all sides by the sheath fluid. If the third inlet is used for introducing sheath fluid, the third inlet is preferably wider than the second inlet, more preferably approximately the same width as the first inlet. Alternatively, a third or additional inlet may be included to, for example, introduce a reagent which chemically reacts with or otherwise modifies a sample already introduced.

The laminar flow channel of the sheath flow module of the present invention can increase in depth at any and/or each inlet. For example, the depth of the channel may be greater between the second inlet junction and the outlet than the depth between the first and second inlet junctions. If a third inlet is present, the depth of the channel between the second and third inlet junctions may be greater than the depth between the first and second inlet junctions but less than the depth between the third inlet junction and the outlet. An increase in depth provides for introduction of an additional fluid layer with retention of all fluid layer dimensions (layers already flowing in the channel, as well as the newly injected layer). This retention of all fluid layer dimensions is preferable, but not necessary.

After all fluids have been introduced and sheath flow has been achieved, the depth of the flow channel can be decreased, leading to vertical hydrodynamic focusing. Optionally, the width of the flow channel can be decreased, leading to horizontal hydrodynamic focusing. The decrease in depth and width can be gradual or abrupt.

The second mode, termed the particle injector mode, is useful in cases in which the center fluid contains particles which are denser or less dense than the fluids surrounding them. In the present invention, one or both fluids may contain particles. If the particles are denser than the fluids surrounding them, the particles settle out of the fluids (gravity pulls the particles down), and hence the particles can elude measurement. In the present invention, this problem of particles settling out of the fluids as a result of gravity can be avoided by orienting the sheath flow module vertically. Alternatively, gravity can be exploited by orienting the module horizontally and positioning the inlets on top of the module. In this mode, particles are injected by first establishing a flow of sheath fluid which is introduced via the first inlet, and then introducing particles or particle-containing center fluid via the second inlet. Because the particles are denser than the center and sheath fluids, gravity acts to center the particles in the vertical dimension. Thus, the second mode of this invention provides for deliberate mix (as a result of gravity) of a center fluid constituent with sheath fluid (which was avoided in the first mode) and allows the particles to be surrounded on all sides by sheath fluid (which was accomplished by a third inlet in the first mode).

If the particles are less dense than the surrounding fluids, they can be injected from the bottom, from whence they float upward as a result of their buoyancy. If the particles are less dense than the surrounding fluids, it may be preferable to introduce a second sheath fluid, via a third inlet, especially if the particles are injected from the top.

In the second mode, the injected particles can be fluorescent beads. It is preferable to have the inlets on the top of the flow channel in this mode. Thus, gravity causes the particles to fall slowly as the fluids flow through the channel. U.S. Pat. No. 5,747,349 issued Mar. 5, 1998, "Fluorescent Reporter Beads for Fluid Analysis," which is incorporated by reference herein in its entirety, discloses reporter beads for chemical analysis of fluid properties such as pH, oxygen saturation and ion content. A fluorescent property of the reporter bead, such as intensity, lifetime or wavelength, is sensitive to a corresponding analyte. Reporter beads are added to a fluid sample and the analyte concentration is determined by measuring the fluorescence of individual beads. Beads tagged with different reporter molecules allow for a plurality of analytes in a sample to be measured simultaneously. Alternatively, absorptive beads tagged with reporter molecules which change absorbance as a function of analyte concentration can be employed in a manner similar to the fluorescent beads.

For use in either mode, the module can include a measurement zone between the most downstream inlet and the outlet. The measurement zone provides optical access for measurements such as scattering, absorbance, fluorescence and emission. The distance between an inlet through which particles are introduced and the outlet is preferably chosen such that, for a given flow speed, the particles do not touch the bottom or top of the flow channel. In the particle injector mode, the measurement zone is preferably positioned so that the particles are surrounded on all sides by fluid and have not dropped so close to the bottom or floated so close to the top of the flow channel that optical measurements are hindered. In a preferred embodiment, optical measurements exploit reflection from the channel walls, as described in U.S. Pat. No. 5,726,751 "Silicon Microchannel Optical Flow Cytometer," issued Mar. 10, 1998.

Prior to the measurement zone, the diameter of the flow channel can taper from a wider to a narrower downstream portion. This narrowing of the channel leads to horizontal hydrodynamic focusing.

The sheath flow module of this invention can be applied to many systems. For example, the sheath fluid may be a sample fluid and the particles in the center fluid may be reporter beads. Alternatively, the sheath fluid may be an inert fluid and the center fluid may be a sample, e.g., blood. These are just a few of the many types of systems in which the present invention can be applied.

The sheath flow module may be made from any etchable, machinable or moldable material, e.g. silicon wafers, plastics, and casting materials.

This invention further provides methods for focusing a center fluid in a sheath fluid using the sheath flow module of the present invention. The methods include introducing a sheath fluid into the first inlet; introducing a center fluid into the second inlet, and optionally introducing a third fluid (which may be sheath fluid) into an optional third inlet. The center fluid may be a sample fluid, and/or may contain reporter beads. The sheath fluid may be a particle-free carrier fluid (optically inert) or it may contain particles. The sheath fluid may be a sample fluid, e.g. whole blood.

BRIEF DESCRIPTION OF THE DRAWINGS

FIG. 5A is a lengthwise section through the center of a sheath flow flow cytometer.

FIG. 5B is a top view of the sheath flow flow cytometer of FIG. 5A.

FIG. 7, comprising

DETAILED DESCRIPTION OF THE INVENTION

The sheath flow module of the present invention provides that a center stream is surrounded on more than one side and optionally on all sides by a sheath fluid. This provides a way to position a particle in the channel. This helps prevent clogging of the flow channel and provides a uniform speed of the particle in the channel. Precise positioning and uniform speed of particles are generally useful in detection schemes, e.g., in flow cytometry.

The term sheath fluid refers to a layer of fluid, which may contain particles, surrounding on more than one side a center fluid. The term center fluid refers to a layer of fluid, which may contain particles, which is surrounded on more than one side by a sheath fluid.

The sheath fluid can be an optically and chemically inert fluid or it can be a sample containing cells and/or analytes of interest.

The center fluid can be a sample fluid which can contain fluorescent reporter beads, and/or cells and/or analytes of interest and/or a chemical indicator and/or a reagent which reacts with an analyte of interest to give a change in detected optical properties. The center fluid can be a non-sample fluid which contains reporter beads, an indicator or a reagent.

The term particles has the common meaning, and refers to undissolved solid matter, and specifically includes cells and fluorescent beads.

Figure 1:
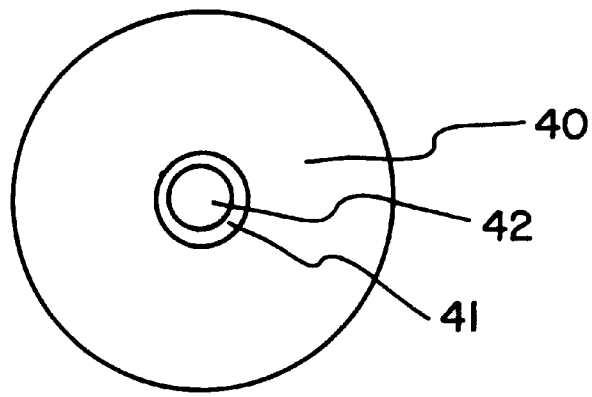
FIG. 1 is a cross section of sheath flow achieved by a known method.
Figure 2:
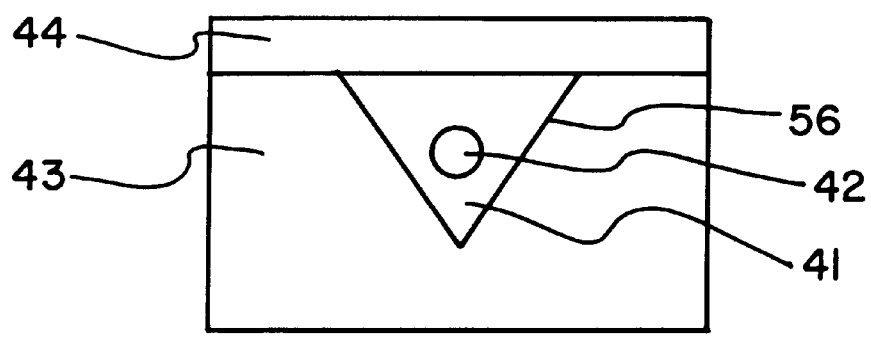
FIG. 2 is a cross section of a v-groove flow channel.

FIG. 2 is a cross section of a v-groove flow channel. A v-groove (56) is etched in a silicon wafer (43) and the channel is sealed by a transparent, e.g. glass, cover plate (44). A particle (42) is surrounded by sample fluid (41).

Figure 3A:
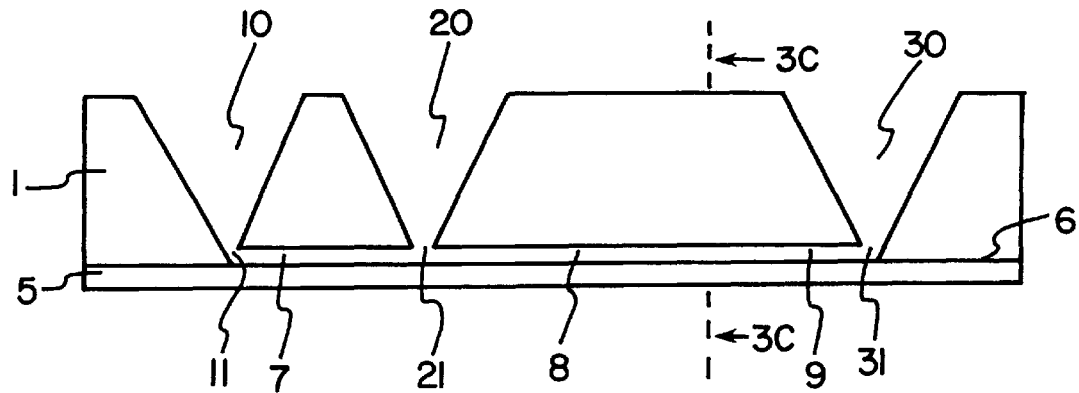
FIG. 3A is a lengthwise section through the center of the sheath flow module of this invention.
Figure 3B:
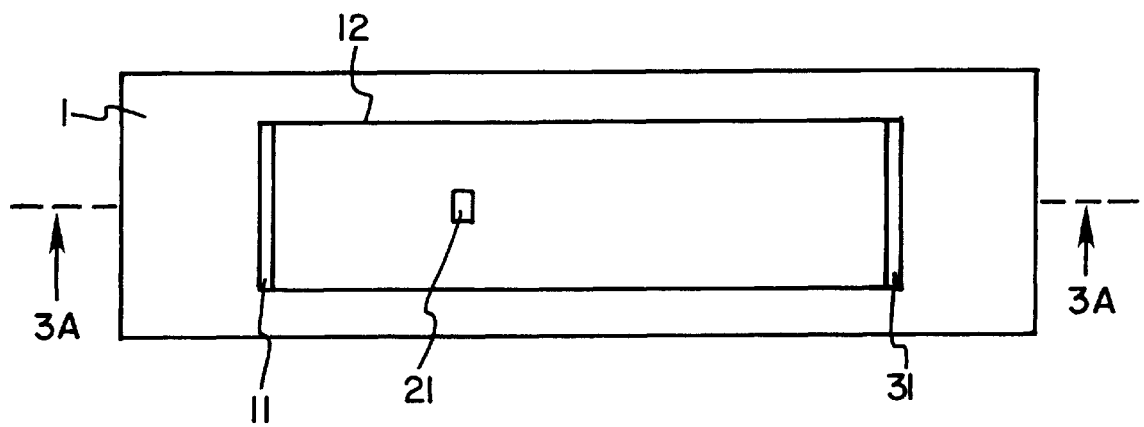
FIG. 3B is a top view of the sheath flow module of this invention.
Figure 3C:
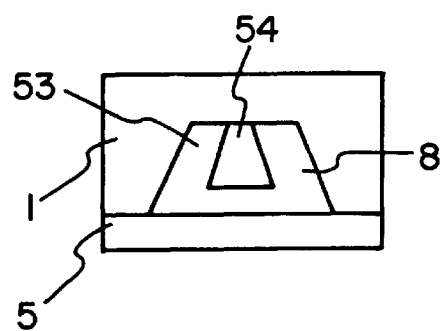
FIG. 3C is a cross section of the flow channel of FIGS. 3A and 3B and sheath flow attained therein.

The sheath flow module of this invention is illustrated in FIGS. 3A, 3B and 3C. FIG. 3A is a lengthwise section through the center of the flow module. Plate (1) is machined, molded or etched to form the flow channel. The plate can be selected from the following which include, but are not limited to, silicon wafers, plastics, e.g. polypropylene, and casting materials. Techniques for etching silicon wafers and molding and machining plastics are well-known in the art.

The plate has at least one surface (6), which is a substantially flat plane. A laminar flow channel (8) is formed in flat plane of the plate. The term laminar flow channel is used herein to refer to a flow channel having dimensions that allow for laminar flow. Surface (6) is termed herein the channel surface. The laminar flow channel has an upstream end (7) and a downstream end (9). A first inlet (10) passes through the plate at the upstream end of the channel and joins the flow channel at first inlet junction (11). An outlet (30) passes through the plate at the downstream end of the channel and joins the flow channel at outlet junction (31). A second inlet (20) passes through the plate between the first inlet and the outlet and joins the flow channel at second inlet junction (21), which is narrower than the first inlet junction. A second plate (5) is sealed to the flat plane of the first plate, thereby forming one side of the laminar flow channel.

A view of the channel surface is illustrated in FIG. 3B. The relative widths of the inlet junctions are shown, as well as the edge (12) of the flow channel (8). The second inlet junction (21) is narrower than the first inlet junction (11).

Referring again to FIGS. 3A and 3B, a sheath fluid is introduced into the flow channel (8) via the first inlet (10) and flows through the flow channel toward the outlet (30). The sheath fluid can be an inert carrier fluid or it can be a sample fluid containing cells, e.g. whole blood, or other analytes. The term carrier fluid is used herein for any fluid used primarily for a hydrodynamic function, and it is typically optically inert and/or chemically inert to the sample being investigated. A center fluid is introduced via the second inlet (20), preferably at lower pressure and speed than the sheath fluid. The center fluid can contain beads and/or cells and/or sample.

FIG. 3C is a cross section of the flow channel of FIGS. 3A and 3B, illustrating the sheath flow attained in one embodiment of the present invention. In this embodiment flow channel (8) is trapezoidal. A center fluid (54), injected from inlet (20), is surrounded on both sides (left and right) and on top by a sheath fluid (53).

The laminar flow channel allows for flow of fluids from the upstream end to the downstream end. The term fluid includes anything which can be included in a laminar flow, including microspheres, liquids and gases.

The fluids are introduced into the inlets by means known in the art, including but not limited to, syringe pumps, electro-osmotic pumps, hydrostatic pressure, and, in general, any micro-pump.

The pressure and speed with which the center fluid is introduced is preferably not greater than the pressure and speed with which the sheath fluid is introduced. Otherwise, the direction of flow through the channel would be undesirably reversed. Preferably, the pressure and speed with which the center fluid is introduced is less than the pressure and speed with which the sheath fluid is introduced. This causes any particles which may be in the center fluid to be spread apart along the long axis of the flow channel, which is called hydrodynamic spacing.

The dimensions of the laminar flow channel of the present invention vary depending on the fluids and sizes of particles flowing through the module. The guiding principle regarding laminar flow channels is that a low Reynolds number be maintained. The Reynolds number is preferably less than about one, and more preferably less than about 0.01.

Fluid dynamic behavior is directly related to the Reynolds number of the flow. The Reynolds number is the ratio of inertial forces to viscous forces. As the Reynolds number is reduced, flow patterns depend more on viscous effects and less on inertial effects. Below a certain Reynolds number, e.g., 0.1, inertial effects can essentially be ignored. The microfluidic devices of this invention do not require inertial effects to perform their tasks, and therefore have no inherent limit on their miniaturization due to Reynolds number effects. The devices of this invention require laminar, non-turbulent flow and are designed according to the foregoing principles to produce flow having low Reynolds numbers, i.e. Reynolds numbers below about 1.

In order to establish laminar flow, the length of the flow channel is preferably at least about five times the particle diameter of the largest particle injected into the flow channel. The term particle diameter is used herein for the longest dimension of the particle. There is no known maximum length of the flow channel. Preferably the length is no greater than a few millimeters. The diameter of the flow channel is preferably about a few microns greater than the diameter of the largest particle injected. The preferred channel diameter is about five times the diameter of the largest particle. Because the Reynolds number depends not only on channel dimension, but also on fluid density, fluid viscosity, fluid velocity and the timescale on which the velocity is changing, the absolute upper limit to the channel diameter is not sharply defined. Although the channel does not, in most cases, have a circular cross section, the term channel diameter is generally used herein for the width at the top of the channel. The maximum width of (any part of) the flow channel is that which still allows for a low Reynolds number and maintains laminar flow. If one of the fluids is blood, the width of the flow channel is preferably about 30–50 microns.

There are two modes of using this invention: a particle injector and a sheath flow mode, depending on the relative densities of the sheath fluid, the center fluid, and any particles in either fluid. If the particles have a different density than the surrounding fluids, then the particle injector mode is utilized. Gravity makes particles denser than the surrounding fluids fall through the fluids and buoyancy makes particles less dense than the surrounding fluids float upward. If the particles are denser than the surrounding fluids, it is preferable to position the inlets on top of the laminar flow channel. If the particles are less dense than the surrounding fluids, it is preferable to position the inlets on the bottom of the laminar flow channel; or if the inlets are on the top, it is preferable to introduce a second layer of sheath fluid via a third inlet.

Alternatively, if the particles and the surrounding fluids are of approximately the same density, herein defined as meaning that the particles stay in the laminar layer in which they began, that is, the particles do not substantially fall or leave the layer they began in, then the sheath flow mode is utilized.

In both modes, the density of a fluid can be changed before injection by methods known to those of ordinary skill in the art. For example, addition of salts changes the density of fluids. Fluids can be mixed to make particles neutrally buoyant.

It is known to those in the art that very small particles, those smaller than about 1–2 microns, will be less affected by gravity than are larger particles. Very small particles are more affected by Brownian motion than by gravity.

Figure 4A:
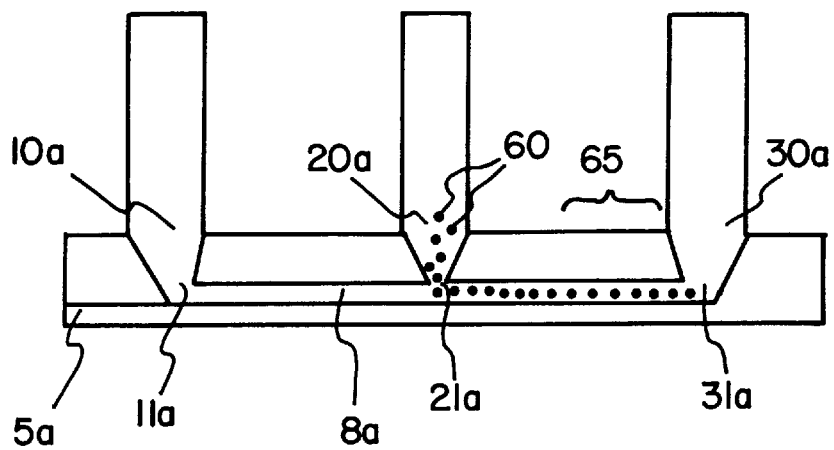
FIG. 4A is a lengthwise section of a particle injector, showing falling particles.
Figure 4B:
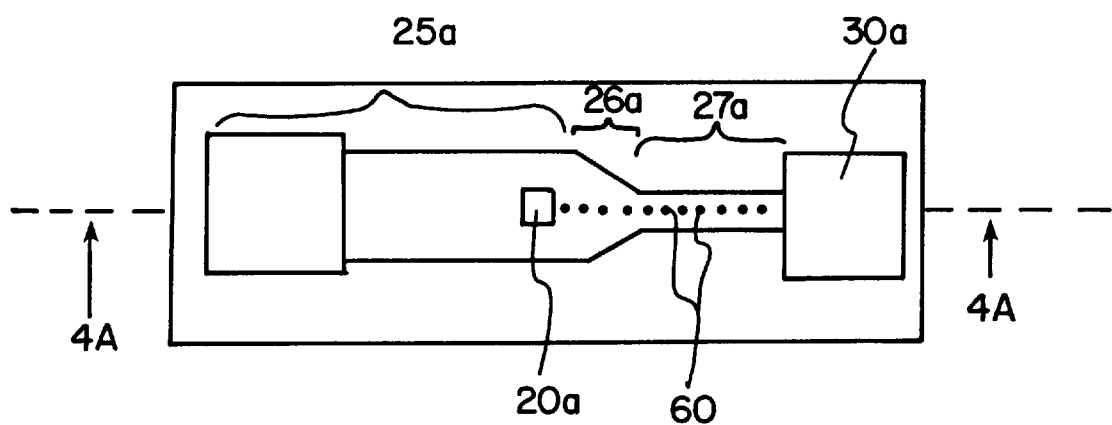
FIG. 4B is a top view of a particle injector, showing the relative widths of inlets and portions of the laminar flow channel.

In the particle injector mode, particles, e.g. cells, bioparticles, microspheres, and fluorescent reporter/indicator beads, are localized in three dimensions in the laminar flow channel. As illustrated in FIG. 4A, a first inlet (10*a*) provides for introduction into the flow channel (8*a*) of a sheath fluid. The sheath fluid can be a sample such as whole blood or other fluid having analytes of interest, or it can be a carrier fluid. The first inlet joins the flow channel at first inlet junction (11*a*). A second inlet (20*a*), which joins the flow channel at second inlet junction (21*a*), provides for introduction of a center fluid which can contain particles (60). As shown in FIG. 4B, the second inlet junction is narrower than the first inlet junction. This provides that the center fluid (and particles therein) entering from the second inlet is surrounded horizontally, i.e., on both sides by the sheath fluid from the first inlet. The center fluid is also surrounded by sheath fluid from below because it is entering downstream of the first inlet. The center fluid is preferably introduced at a lower pressure and lower speed than the pressure and speed of the sheath fluid, thereby spacing apart the particles in the center fluid (hydrodynamic spacing).

In one embodiment, the laminar flow channel has a first width at an upstream portion, a second, narrower width at a downstream portion, and a tapered portion connecting the upstream and downstream portions. This tapering of the flow channel allows for horizontal hydrodynamic focusing of the laminar fluids flowing through the sheath flow module. The particles flow in a single file fashion through the narrow portion, thereby facilitating optical measurements of the particles, such as fluorescence and light scattering measurements. In FIG. 4B, the upstream portion (25*a*) is connected to the downstream portion (27*a*) via the tapered portion (26*a*). In this embodiment the second inlet is positioned in the upstream portion. It can alternatively be in the tapered portion. It is preferable to position the second inlet in the upstream portion because this allows for greater and more precise horizontal hydrodynamic focusing.

In the particle injector mode, vertical centering is accomplished by gravity. The measurement zone (65) is preferably positioned after the tapered portion at a point where the beads are surrounded by sheath fluid in all directions, i.e., so that they have fallen preferably about half-way from the top to the bottom of the flow channel or floated about half-way from the bottom to the top of the flow channel.

The injected particles can be reporter beads and either the center fluid or the sheath fluid can be a sample fluid such as blood. Each reporter bead comprises a substrate bead having a plurality of absorptive or fluorescent reporter molecules immobilized thereon. The absorption or fluorescence of the reporter molecules is sensitive to the concentration of an analyte in the sample fluid. The term substrate bead is used herein for a particle which can be dispersed in a sample fluid and which can immobilize reagents, separate from the sample fluid. The term reporter molecule is used herein for an absorptive or fluorescent molecule which changes color (changes wavelength of maximum absorption) or fluorescence properties, respectively, as a function of the concentration of a particular analyte or class of analytes. Many dyes and fluorochromes known in the art can be used as reporter molecules in this invention (see, for example, R. P. Haugland, Handbook of Fluorescent Probes and Research Chemical, 5th Edition, Molecular Probes Inc., Eugene, 1992).

The reporter molecules interact with the analyte in a way that changes the fluorescent properties of the reporter molecule. In some instances, the reporter molecule reacts with the analyte, as in the case of albumin detection by AB 580 (Molecular Probes). In some cases the interaction is not a chemical reaction. For example, the reporter molecule fluorescence can be quenched by nonradiative energy transfer to the analyte, as in the case of $O_2$ detection by ruthenium diphenyl phenanthroline. For some reporter molecules the fluorescence is sensitive to polarity changes in the fluid, which can be used to detect organic solvents and hydrocarbons within an aqueous fluid. The interaction can also be through other solvent effects, wherein the ionic strength of the solvent affects the fluorescence. Solvent effects can be used to determine the total concentration of all dissolved ions. The interaction preferably does not lead to an aggregate with other particles and, in particular, does not create an aggregate containing a plurality of reporter beads. It is preferred that the interaction of the analyte with the reporter molecules does not significantly perturb the analyte concentration in the fluid.

The beads can be of approximately the same or different density compared to the sheath and center fluids. If the beads are denser than the sheath and center fluids, gravity will cause the beads to fall slowly toward the bottom of the flow channel. Hence, the measurement zone is preferably positioned such that optical measurements are performed before the beads have fallen to the bottom of the channel.

More than one type of bead or particle, e.g. cells, can be monitored. Particles of different densities fall at different rates toward the bottom of the flow channel. The differences in density can be used to discriminate between or among various types of particles. If particles of substantially different densities are to be monitored, more than one measurement zone is preferable.

In general, the sheath flow module can be used in a horizontal position, that is, with the long axis of the flow channel parallel to the ground. However, the sheath flow module may be tilted or held vertically to counteract the effect of gravity. For example, if the particles are falling faster toward the bottom of the flow channel than desired and therefore reaching the bottom before being interrogated in the measurement zone, it may be preferable to tilt the module so that the downstream end is lower than the upstream end. It may be preferable to counteract even more strongly the effect of gravity which pulls the particles toward the bottom of the flow channel by using the sheath flow module in a vertical position, that is, with the upstream end directed straight up and the downstream end directed straight down.

An example of using the invention in the particle injector mode is the following. The sheath fluid can be whole blood and the center fluid can be a buffered solution containing fluorescent reporter beads. In this example, whole blood is injected via the first inlet and thus is the sheath fluid. The center fluid containing fluorescent reporter beads is injected via the second inlet, preferably at a volume flow rate less than the sheath fluid, thereby leading to hydrodynamic spacing of the beads. The beads are in the center fluid. The beads are completely surrounded by fluid and therefore do not get stuck in the flow channel. The beads, preferably being denser than the sheath and center fluids, slowly drop through the sample, which in this case is the whole blood sheath fluid.

The flow channel may preferably taper, a wider upstream portion tapering to a narrower downstream portion, thereby leading to horizontal hydrodynamic focusing. In the example wherein the sheath fluid is whole blood, the tapering provides single file particle flow through the measurement zone so that the cells do not cause optical interference with the reporter beads. This horizontal tapering can be accompanied by a decrease in the depth of the flow channel. With enough tapering, the channel becomes narrow enough (in both width and depth) that only single file particles can pass through it. Hence, in the measurement zone, red blood cells, white blood cells, reporter beads and any other particles (which might result from shearing of cells) are detected and identified by light scattering and fluorescence measurements.

Another example of using the present invention as a particle injector is to introduce via the first inlet a carrier fluid as the sheath fluid. A center fluid containing a sample is introduced via the second inlet. A third inlet, preferably joining the channel at a narrow inlet junction, provides for introduction of a third fluid containing fluorescent reporter beads which drop into the center fluid and interact with analytes therein.

Yet another example of using the present invention as a particle injector is to introduce a carrier fluid as the first sheath fluid via the first inlet and then to introduce a solution containing the sample of interest and fluorescent reporter beads via the second inlet. Optionally, a second sheath fluid may be introduced via a third inlet. As above, the beads react with an analyte in the sample, allowing for determination of analyte concentrations.

In another mode, the sheath flow module of the present invention can function to prepare a sheath flow wherein gravity is not a primary consideration. FIG. 5A is a lengthwise section through the center of the flow module. A first sheath fluid, typically an inert carrier fluid such as buffered water, is introduced via the first inlet (10b). The first inlet joins the laminar flow channel (8b) at first inlet junction (11b). A center fluid, typically a sample such as whole blood, is introduced via the second inlet (20b) which joins the flow channel at second inlet junction (21b). In this embodiment a third inlet (40) can be included, for example, to introduce a second sheath fluid, joining the laminar flow channel (86) at junction 41 so that the center fluid is concentrically surrounded by sheath fluid. The depth of the flow channel can increase at the second inlet junction and again at the third inlet junction, as illustrated in FIG. 5A. An increase in depth of the flow channel at an inlet junction is preferable, but not necessary. Such an increase can preserve the fluid layer dimensions. In the absence of such an increase in depth, the fluid layers are thinner and flow faster than when the channel depth is increased.

Figure 5C:
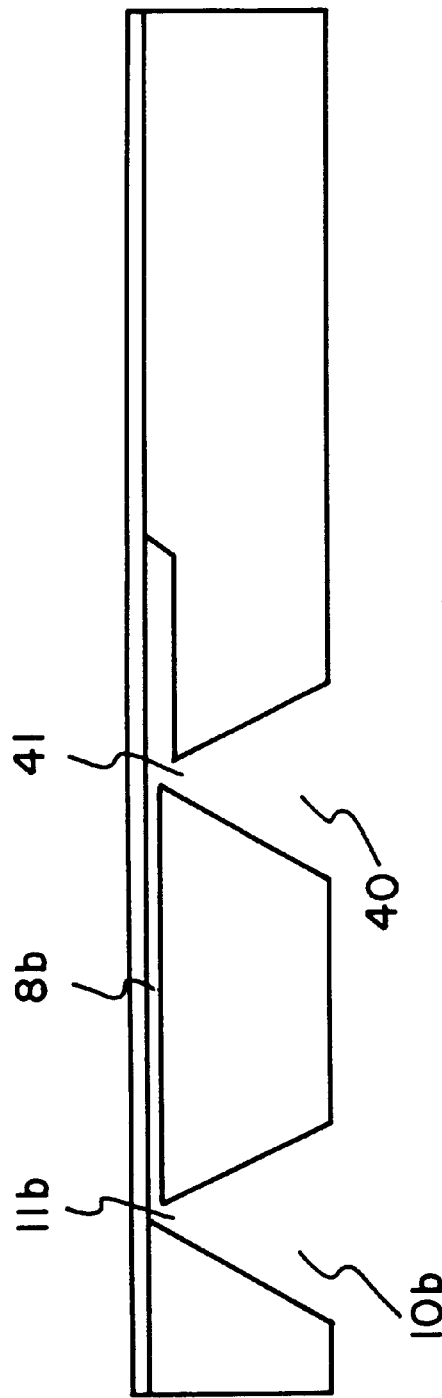
FIG. 5C is a lengthwise section through the flow channel some distance from the center, i.e. not through the second inlet, in the flow channel of FIGS. 5A and 5B in which the depth of the channel increases at the second inlet only across the width of the second inlet and increases across the entire width of the channel at the third inlet.

The increase in channel depth at an inlet can be across the entire width of the flow channel, or the depth can increase only across the width of the inlet junction at which said increase in depth begins. FIG. 5C is a lengthwise section through the flow channel some distance from the center, i.e., a section which does not pass through the second inlet junction, in an embodiment where the depth of the flow channel increases only across the width of the second inlet junction and also at the third inlet junction across the entire width of the flow channel.

Figure 6:
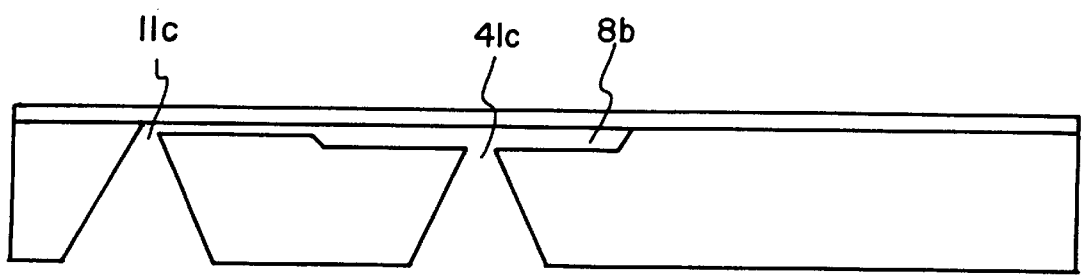
FIG. 6 is a lengthwise section through the flow channel some distance from the center, i.e. not through the second inlet, in an alternative embodiment to the flow channel of FIGS. 5A–5D.

FIG. 6 is a lengthwise section of an alternative embodiment wherein the depth of the flow channel increases at the second inlet junction (not shown) and third inlet junction (41c) across the entire width of the flow channel; this section is some distance from the center, i.e., it does not pass through the second inlet junction (and the third inlet junction is wider than the second).

The size of the increase in depth of the flow channel can vary, as long as the flow behavior in all parts of the flow channel is laminar, i.e., a low Reynolds number is maintained. In general, an object of the invention is to prevent particles from touching the walls/sides and bottom and top (second plate, e.g. transparent cover) of the flow channel. Thus, in general, the preferable minimum increase in depth is approximately the diameter of the largest particle in the channel.

Referring to FIGS. 5A and 5B, the flow channel may include an upstream portion (25b) which is connected via a tapered portion (26b) to a narrower downstream portion (27b). As in the particle injector mode, the tapering (narrowing of the width) may or may not occur in conjunction with a decrease in depth of the flow channel. That is, the flow channel may be designed for horizontal and/or vertical hydrodynamic focusing. In the illustrated embodiment the depth also decreases in section 26b.

Figure 5D:
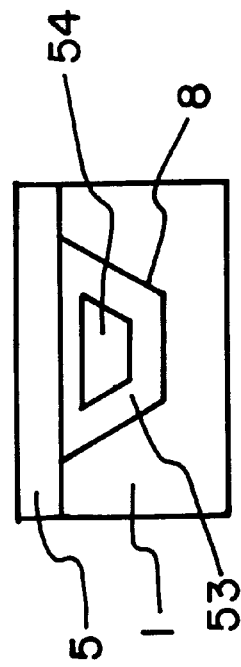
FIG. 5D is a cross section of the fluid flowing in the flow channel of FIGS. 5A, B and C.

FIG. 5D is a cross section of the flow channel of FIG. 5B sheath flow attained by it. In this embodiment flow channel (8) is trapezoidal. A center fluid (54), introduced from inlet (20b), is surrounded on all sides by a sheath fluid (53) introduced from inlets (11b) and (41). The channel (8) is formed in the plate (1) and sealed with a transparent, e.g. glass, cover (5).

Figure 7A:
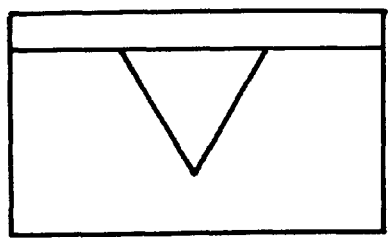
FIGS. 7A–7D, shows cross sections of various embodiments of the flow channel of this invention.
Figure 7B:
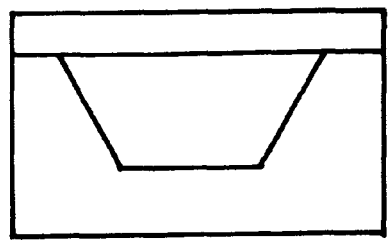
Figure 7C:
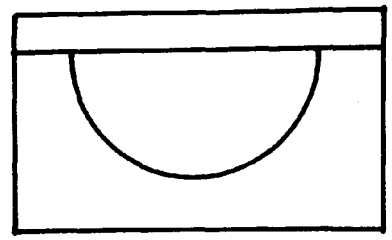
Figure 7D:
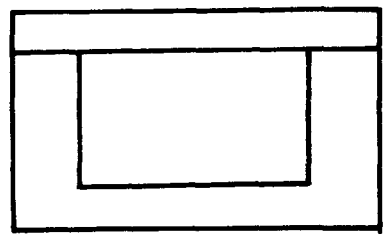

FIGS. 7A–7D show cross sections of various embodiments of the flow channel of the present invention, e.g. the flow channel of FIGS. 3A and 3B. If the plate is silicon, etching with certain wet anisotropic etchants, e.g., ethylene diamine pyrocatechol, leads to either a v-groove (FIG. 7A) or a trapezoidal (FIG. 7B) cross section, depending on the etch time. The v-groove and trapezoidal cross sections are particularly suited to optical measurements exploiting reflection from the channel wall. Other etchants and methods can be used with silicon to yield a variety of cross sections. If the plate is a moldable material, e.g. a plastic, the cross section is not limited. It can be whatever shape is most convenient for the intended application. If the flow module is made of a transparent material, optical measurements can be made in transmission rather than reflection, and planar, sloping channel walls are not required. FIGS. 7C and 7D show examples of usable cross sections.

The following are examples of how to use this invention in the sheath flow mode.

The methods of this invention for creating a flow having a center fluid in a sheath fluid include introducing a carrier sheath fluid into the flow channel via the first inlet, and introducing a sample fluid of approximately the same density, which is the center fluid, via the second inlet. Optionally, a carrier sheath fluid can be introduced via a third inlet also.

Alternatively, methods for creating a flow having a center fluid in a sheath fluid include introducing a carrier sheath fluid into the flow channel via the first inlet, and introducing a sample fluid containing reporter beads of approximately the same density as the sample, which is the center fluid, via the second inlet. Optionally, a carrier sheath fluid can be introduced via a third inlet also. For example, this invention provides a method for focusing a sample fluid, e.g. whole blood, which has been mixed with reporter beads, by introducing a carrier sheath fluid via the first inlet and a solution containing the sample and beads via the second inlet. Optionally, another layer of carrier sheath fluid may be introduced via a third inlet. One or more analytes in the sample react with the beads, which are prevented from touching the walls/sides of the flow channel by the sheath flow created by this method of focusing. Optical measurements can be performed in the measurement zone.

Another example is that of introducing a sheath fluid containing a reagent into the flow channel via the first inlet, and introducing a sample fluid of approximately the same density, which is the center fluid, via the second inlet. Optionally, a sheath fluid containing a reagent can be introduced via a third inlet also.

The methods of this invention for creating a flow having a center fluid in a sheath fluid further include introducing a carrier fluid as the first sheath fluid into the flow channel via the first inlet, and introducing a sample fluid of approximately the same density, which is the center fluid, via the second inlet. Optionally, a second sheath fluid containing a reagent can be introduced via a third inlet.

Another method for creating a flow having a center fluid in a sheath fluid is that of introducing a carrier sheath fluid into the flow channel via the first inlet, and introducing a sample fluid containing reporter beads of approximately the same density as the sample, which is the center fluid, via the second inlet. Optionally, a sheath fluid containing a reagent can be introduced via a third inlet also.

Another example of an application of the sheath flow module of the present invention is the following. A sample of blood is injected via the first inlet. A chemical indicator, which is either dissolved or isolated on reported beads, is injected via the second inlet to form a center fluid, into which small analytes from the sample diffuse and react with the indicator. Another layer of blood can be injected via a third inlet, so that the center fluid is completely surrounded by a sheath of blood. Hydrodynamic focusing leads to a single file flow of particles through the downstream portion of the channel where optical measurements can be performed. The laminar flow of the solution prevents mixing other than diffusion. Small analytes in the blood, for example $O_2$ or calcium ions, can however, diffuse to the center fluid to react with the reporter molecules. U.S. Pat. No. 5,716,852 issued Feb. 10, 1998, for "Microfabricated Diffusion-Based Chemical Sensor," which is incorporated in its entirety by reference herein, discloses microsensors and methods for exploiting diffusion to analyze the presence and concentration of small particles (analytes) in streams containing both these small particles and larger particles.

Figure 11:
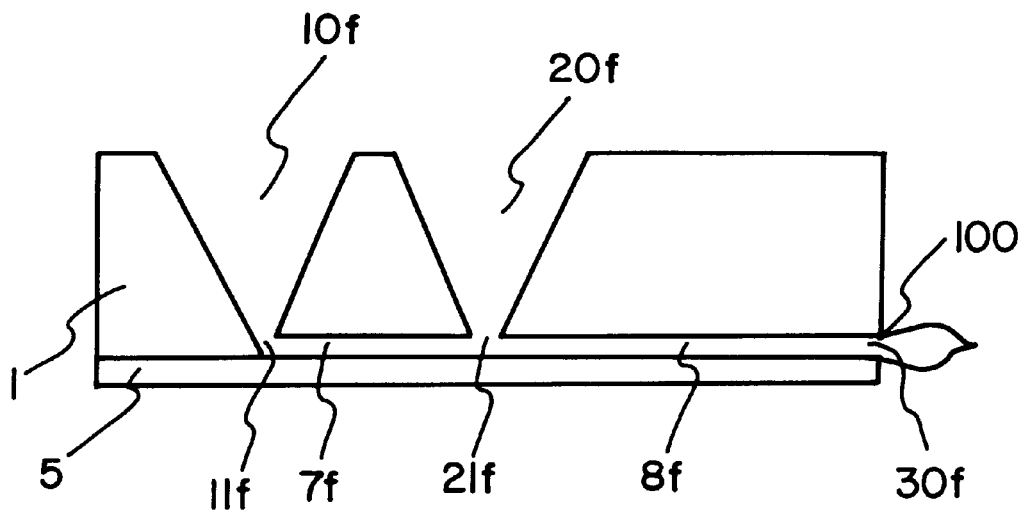
FIG. 11A shows the sheath flow module creating a flame.
FIG. 11B shows the sheath flow module with an outlet at the downstream end of the channel for introducing particles into a flame for emission spectroscopy.
Figure 11:
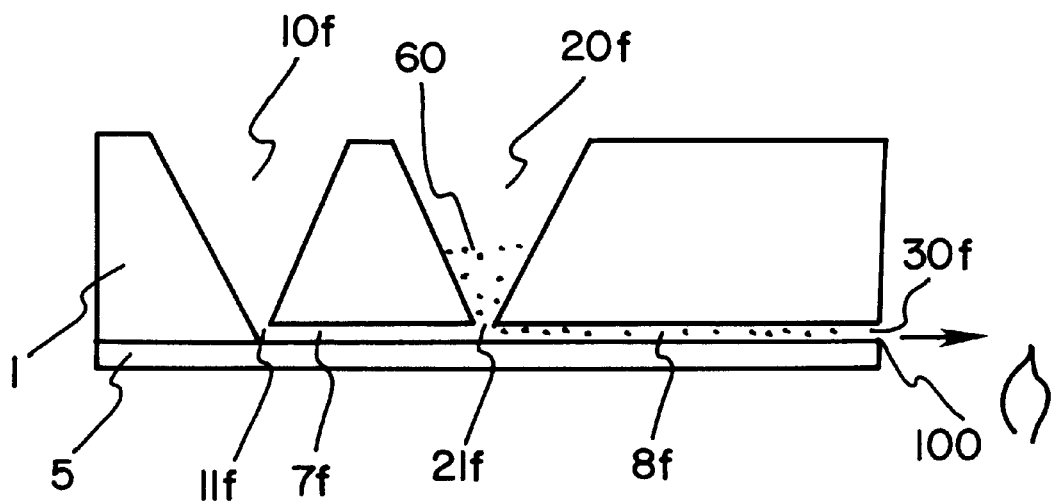

Another application of the sheath flow module is the formation of a flame with two temperatures, e.g. an inner, hotter core, surrounded by an outer, cooler sheath of flame. When employed for this purpose, the downstream end of the channel is an outlet to air, as illustrated in FIG. 11A. FIG. 11A shows the fluids combusting and thereby forming a flame at outlet (30f) at the downstream edge (100) of the plate. This type of flame can be formed by introducing a relatively cooler burning liquid or gas into the flow channel (8f) via the first inlet (10f). A higher temperature burning liquid or gas is introduced via the second inlet (20f). Alternatively, a lower temperature burning liquid or gas is introduced via the second inlet (20f). Optionally, the relatively cooler burning liquid or gas is also introduced via a third inlet (not shown). The higher temperature burning liquid or gas is surrounded by the cooler temperature burning liquid or gas, forming a laminar flame. A sheath flow module used for creating flames in this embodiment is made from appropriate material, e.g., material which does not melt or burn at the temperatures of the flame formed thereby, for example certain metals.

The sheath flow module of the present invention also has applications in the field of emission spectroscopy. When employed for this purpose also, the downstream end of the channel is an outlet to air. As FIG. 11B shows, the device of this invention provides a vehicle for transporting/introducing solids into a flame. In the device of FIG. 11B a sheath fluid is introduced via first inlet (10f) and solid particles suspended in a fluid via second inlet (20f). The fluid and particles flow through the flow channel (8f) and are introduced to a flame upon exiting the channel at outlet (30f) at downstream edge (100) of the plate. The fluids are injected with enough pressure that they spray out, indicated by the arrow, of the channel at outlet (30f) and into a flame, e.g., a plasma torch. Upon vaporization in the flame, an emission spectrum of the particles can be obtained. In general, prior to the present invention, it has been necessary to dissolve a substance before introducing it into a flame. However, the present invention can be used to inject solid particles into a flame. The sheath flow module of this invention can be used to determine the concentration of solid analytes or contaminants, e.g., heavy metals, in a sample. A sample containing contaminants, e.g. lead, or other analytes can be injected into a sheath fluid, which is then introduced into a flame. An emission spectrum indicates the concentration of lead or other analyte in the sample.

In all of these examples horizontal and/or vertical focussing is possible. The following considerations can be helpful. For example, in the sheath flow mode, if fluorescence or absorbance of a fluid, as opposed to a particle, is being measured, it may be preferable to avoid vertical focusing. In this case, because the fluorescence and/or absorbance may be small, it may be preferable not to decrease the channel depth because doing so would decrease the amount of fluid for optical measurement. Hence, it may be preferable to focus only horizontally in a case like this. On the other hand, if optical measurements are being performed on particles, e.g. cells or reporter beads, it may be preferable to hydrodynamically focus both vertically and horizontally in order to attain a single file flow of particles through the measurement zone. In this case, the degree of fluorescence, absorbance, or scattering, etc. for a given particle is a function of analyte concentration and is independent of path length; therefore, vertical focusing need not be avoided for that reason.

This invention also includes methods of using the sheath flow module, as described above.

U.S. Pat. No. 5,932,100 "Microfabricated Differential Extraction Device and Method," issued Aug. 3, 1999, which is incorporated in its entirety by reference herein, discloses a microfabricated device which has branching flow channels. The branching allows for separation of the laminar fluid into two or more channels. This is desirable in some cases, e.g. if one stream is an indicator stream and the other stream is a sample like whole blood. In this case, it can be desirable to perform optical measurements on the indicator stream only, after analytes in the sample have diffused into the indicator stream. Splitting the flow channel into two or more branches provides for this.

Figure 9:
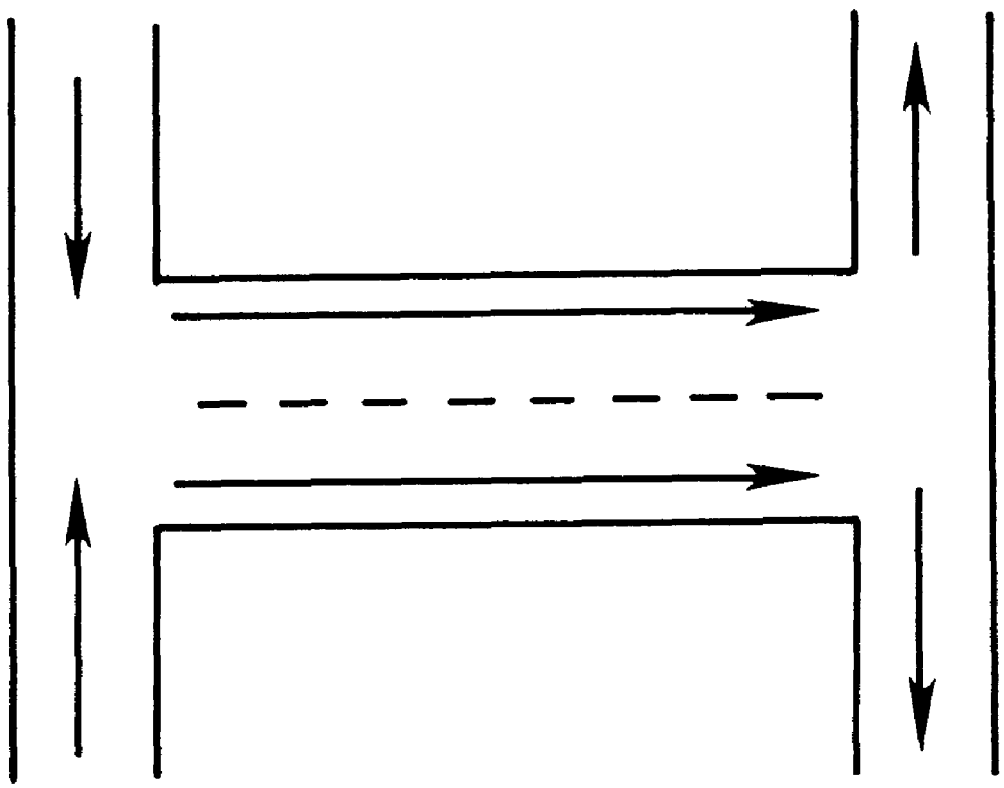
FIG. 9 illustrates the channels of an embodiment of the "H" filter of U.S. Pat. No. 5,932,100 issued Aug. 3, 1999.

The microfabricated device of U.S. Pat. No. 5,932,100, in its simplest concept, is illustrated by a device comprising microchannels in the shape of an "H". FIG. 9 illustrates an embodiment of the "H" filter. FIG. 9 shows the splitting of the flow channel, into two branching flow channels and the laminar fluid therein branching into two streams.

Figure 10A:
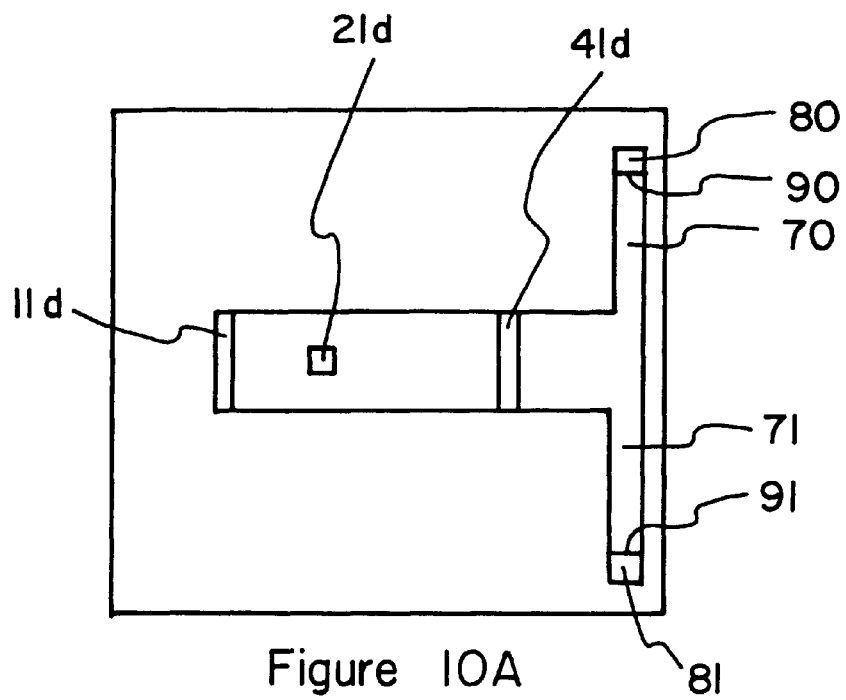
FIG. 10A illustrates a sheath flow module, having a branching flow channel.

The principle of the "H" filter can be used in conjunction with the sheath flow module of the present invention. This is useful in applications wherein it is preferable to split the fluids flowing in the flow channel into two or more streams. For example, a sheath flow module can be provided with a first branching flow channel (70) and a second branching flow channel (71), as in FIG. 10A. An outlet is provided at the terminal end of each branching flow channel. Outlet (80) is at the terminal end (90) of branching flow channel (70), and outlet (81) is at the terminal end (91) of branching flow channel(71).

Figure 10B:
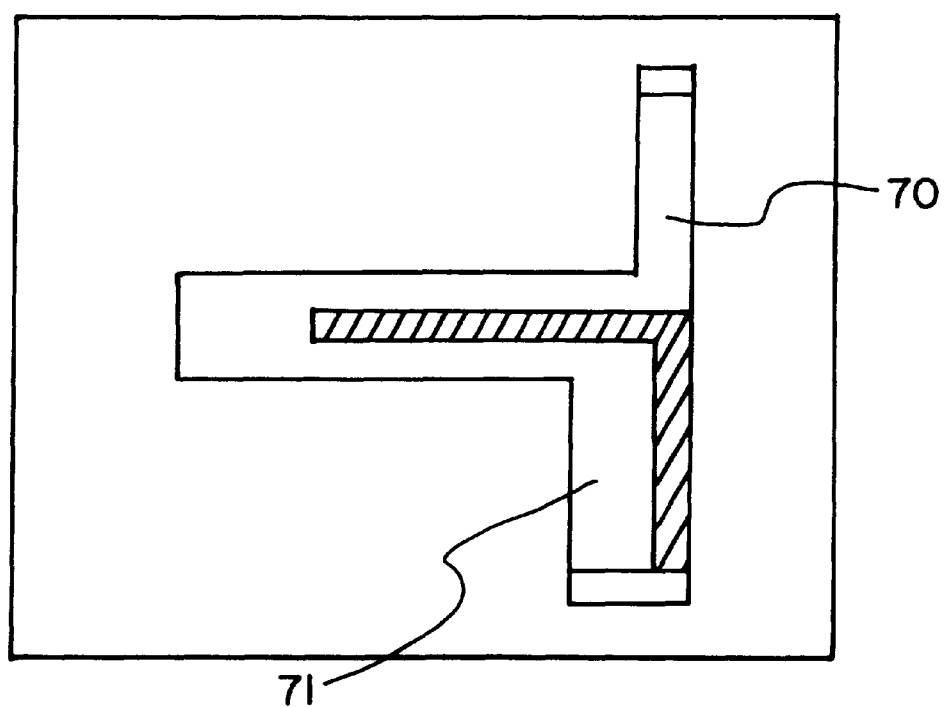
FIG. 10B illustrates the use of a branching flow channel to divide the fluid flowing through the flow channel.
Figure 10:
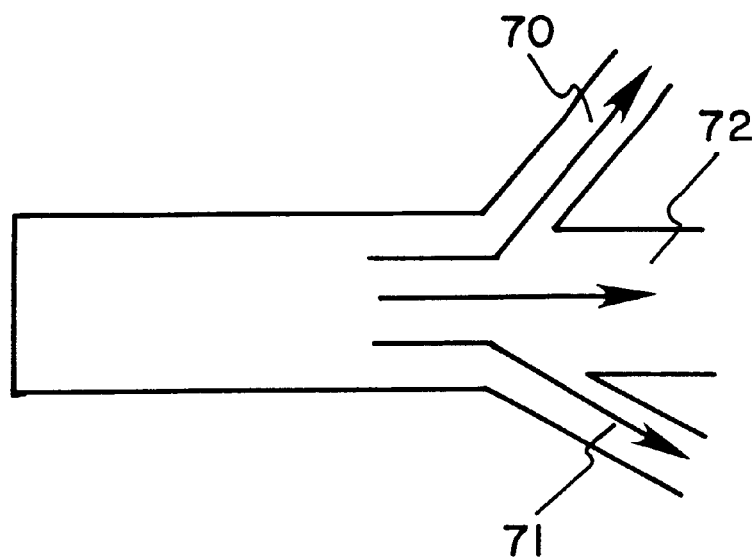
FIG. 10C shows the branching flow channels of a sheath flow module.
FIG. 10D shows that the branching flow channels may join the flow channel at angles other than 90 degrees.
Figure 10:
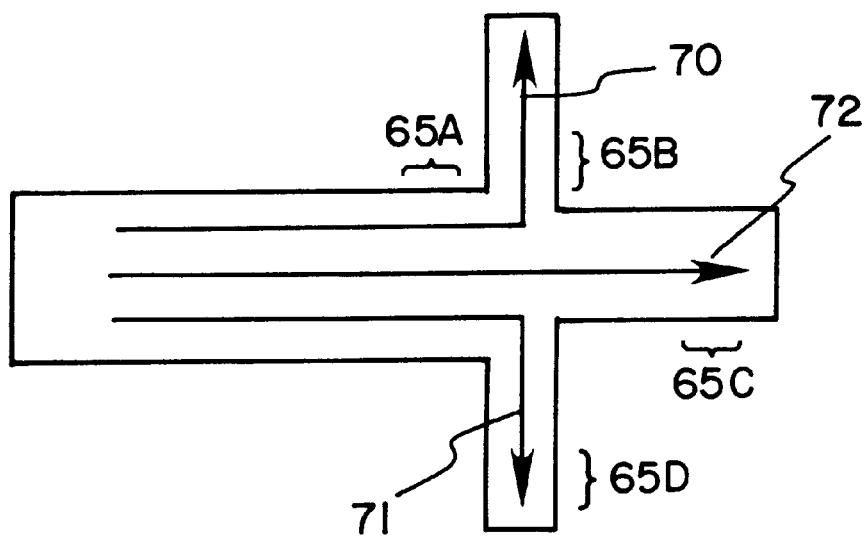

The sheath flow module of the present invention can include a flow channel which splits into two or more branching flow channels. The fluid flowing through the flow channel is then diverted into the branching flow channels as illustrated in FIG. 10B. In this case, the center fluid flows into branching flow channel (71) and the sheath fluid flows into branching flow channel (70). Because sheath fluid is above, below, and to the side of the center fluid, some sheath fluid will also be diverted into branching flow channel (71). If the branching flow channels are of approximately the same diameter, approximately half of the sheath fluid and half of the center fluid is diverted into each branching flow channel. The branching flow channels can be positioned and made the appropriate size to divert desired portions of the fluid into each branching flow channel, e.g., one branching flow channel may receive only sheath fluid while another branching flow channel may receive both sheath fluid and center fluid.

The sheath flow module of the present invention can be split into two or more branching flow channels, either upstream or downstream of the measurement zone(s). For example, in a channel split into three branching flow channels, the measurement zone(s) is/are positioned either upstream of the split and/or after the flow channel splits, as illustrated in FIG. 10C which shows the measurement zone at 65A, 65B, 65C and/or 65D. The arrows indicate fluid flow.

The streams can be split/separated at any arbitrary location by precise regulation of the flow rate at the branching flow channels (e.g., 70, 71, and 72 in FIG. 10C). It may be preferable to split the channel upstream of the measurement zone in cases wherein a sheath fluid contains particles or other materials which might interfere with optical measurements. In such a case, the measurement zone (65C) on branching flow channel (72) in FIG. 10C would provide measurements of the center fluid, as the sheath fluid on the sides of the center fluid would be diverted into branching flow channels (70) and (71).

The sheath flow module of this invention which includes branching flow channels is also used to separate small analytes and particles from larger ones. For example, in a case wherein the sheath fluid is an inert carrier and the center fluid is whole blood, small analytes, e.g., carbon dioxide, diffuse from the center fluid into the sheath fluid. After diffusion of carbon dioxide from the blood to the sheath fluid, the sheath fluid containing carbon dioxide is then diverted into branching flow channels (70) and (71) and can be optically measured at measurement zones 65B and 65D of FIG. 10C. The center fluid, containing larger particles, e.g., blood cells, flows through branching flow channel (72).

FIG. 10D shows another embodiment of the sheath flow module of this invention which includes branching flow channels. The branching flow channels do not necessarily join the flow channel at 90 degree angles. The angle at which the branching flow channels join with the flow channel is not limited.

Numerous embodiments besides those mentioned herein will be readily apparent to those skilled in the art and fall within the range and scope of this invention. All references cited in this specification are incorporated in their entirety by reference herein. The following examples illustrate the invention, but is/are in no way intended to limit the invention.

EXAMPLES

Example 1

A stream containing 0.1 M HEPES pH 7 buffer and 0.1% per volume fluorescent beads (0.05 microns) was injected in the first inlet of a sheath flow module at a flow speed of 50 nL/sec. The channel cross section was 400 $\mu$m by 50 $\mu$m. The small fluorescent beads were included in the sheath fluid in order to visualize the fluid flow. 0.1 M HEPES pH 7 buffer, were injected into the sheath fluid at a flow speed of 10 nL/sec via the second inlet. The second inlet was in the tapered portion of the module. A fluorescence micrograph showed the larger beads falling out of the second inlet into the sheath fluid and being hydrodynamically spaced. The larger beads did not stick together. They flowed in single file through the measurement zone.

Example 2

Figure 8A:
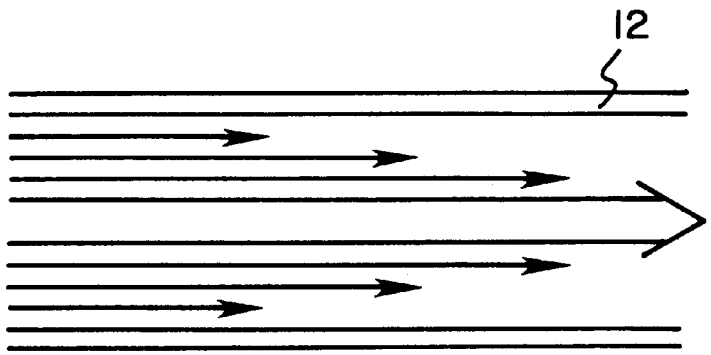
FIG. 8A shows the relative velocities of the various layers of fluids in the laminar flow channel.

FIG. 8A shows the expected relative velocities of the various layers of fluids in the laminar flow channel. The closer to the center, the faster the fluid flows.

Figure 8B:
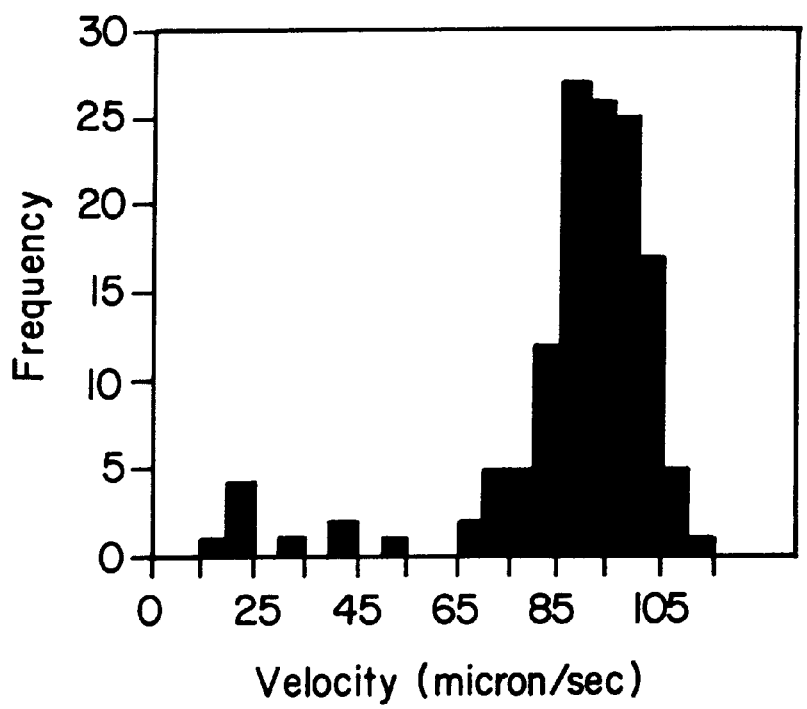
FIG. 8B is a velocity histogram of fluorescent beads in a sheath flow channel. Frequency (a measure of the number of beads) versus velocity of the beads is graphed.

FIG. 8B is a velocity histogram of an experiment utilizing the sheath flow module of the present invention with fluorescent beads in the center fluid of the sheath flow channel. A carrier fluid was introduced via a first and third inlet, and fluorescent reporter beads were introduced via a second inlet. Frequency (a measure of the number of beads) versus velocity of the beads is graphed. The solid line represents the expected distribution of beads if the beads were uniformly distributed across the channel. The histogram shows that most of the beads were traveling at relatively fast velocities.

The observed distribution was concentrated near the maximum velocity, indicating that the beads are localized in the center fluid.

We claim:

1. A sheath flow module, comprising:
   a plate having formed therein:
   a laminar flow channel formed in a first surface of said plate, said flow channel comprising an upstream end and a downstream end;
   a first inlet passing through said plate and forming a first inlet junction with said upstream end of said channel;
   an outlet passing through said plate and forming an outlet junction with said downstream end of said channel;
   a second inlet passing through said plate and forming a second inlet junction with said channel, narrower than said first inlet junction, between said first inlet junction and said outlet junction;
   wherein said laminar flow channel does not decrease in depth downstream from said second inlet junction; and
   a first fluid and a second fluid flowing in laminar flow within said laminar flow channel such that said first fluid is in laminar flow with said second fluid, said sheath flow module being constructed and arranged such that said second fluid is surrounded on at least two sides by said first fluid.

2. The sheath flow module of claim 1 further comprising a plurality of additional inlets passing through said plate and forming a plurality of junctions with said channel between said second inlet and said outlet.

3. The sheath flow module of claim 1 wherein said flow channel has a first width in an upstream portion starting at said upstream end, a second, narrower, width in a downstream portion ending at said downstream end, and a tapered portion connecting said upstream portion to said downstream portion, and wherein said second inlet is in said upstream portion or said tapered portion of said channel.

4. The sheath flow module of claim 1 further comprising a third inlet passing through said plate and forming a third inlet junction with said channel between said second inlet and said outlet.

5. The sheath flow module of claim 4 wherein said third inlet junction is wider than said second inlet junction.

6. The sheath flow module of claim 4 wherein said third inlet junction is approximately the same width as said first inlet junction.

7. A method of completely surrounding a center fluid with a sheath fluid, comprising the steps of:
   providing the sheath flow module of claim 4,
   injecting a first sheath fluid into said first inlet through said first inlet junction into said laminar flow channel and a second sheath fluid into said third inlet through said third inlet junction into said laminar flow channel; and
   injecting a center fluid into said laminar flow channel via said second inlet through said second inlet junction, whereby said sheath fluid completely surrounds said center fluid.

8. The method of claim 7 wherein said center fluid is a sample fluid.

9. The method of claim 8 wherein the densities of said first and second sheath fluids and said sample fluid are approximately equal.

10. The method of claim 7 wherein said first and second sheath fluids are a carrier fluid and said center fluid is a sample.

11. The method of claim 7 wherein said first and second sheath fluids and said center fluid are of approximately equal densities.

12. The method of claim 7 wherein said first sheath fluid is a carrier fluid, said center fluid is a sample, and said second sheath fluid is a reagent.

13. The method of claim 12 wherein said carrier fluid, said sample, and said reagent are of approximately equal densities.

14. The method of claim 7 wherein said first and second sheath fluids are a carrier fluid and said center fluid is a sample fluid containing reporter beads.

15. The method of claim 14 wherein said carrier fluid and said sample fluid are of approximately equal densities.

16. The method of claim 7 wherein said first sheath fluid is a carrier fluid, said center fluid is a sample containing reporter beads, and said second sheath fluid is a reagent.

17. The method of claim 16 wherein said carrier fluid, said sample, and said reagent are of approximately equal densities.

18. A method of surrounding a center fluid stream on at least two sides by a sheath fluid, comprising the steps of:
   providing the sheath flow module of claim 1;
   injecting a sheath fluid via said first inlet through said first inlet junction into said laminar flow channel; and
   injecting a center fluid into said laminar flow channel via said second inlet through said second inlet junction whereby said sheath fluid surrounds said center fluid on at least two sides thereof.

19. The method of claim 18 wherein said center fluid is a sample fluid.

20. The method of claim 19 wherein said sheath fluid is a carrier fluid.

21. The method of claim 18 wherein the sheath fluid is a sample fluid and said center fluid is an indicator fluid.

22. The method of claim 18 wherein the densities of said sample fluid and said indicator fluid are approximately equal.

23. The sheath flow module of claim 1 comprising a transparent second plate sealed to the first surface of said plate.

24. The sheath flow module of claim 23 further comprising a measurement zone between said second inlet and said outlet.

25. The sheath flow module of claim 24 wherein said plates are transparent in said measurement zone, thereby allowing for optical measurements by transmission.

26. The sheath flow module of claim 24 wherein said plate is a reflective material and said second plate is transparent in said measurement zone, thereby allowing for optical measurements by reflection.

27. The sheath flow module of claim 26 wherein said channel is a v-groove flow channel in said measurement zone.

28. The sheath flow module of claim 27 wherein said plate is silicon.

29. A sheath flow module, comprising:
   a plate having formed therein:
   a laminar flow channel formed in a first surface of said plate, said flow channel comprising an upstream end and a downstream end wherein said flow channel has a first width in an upstream portion starting at said upstream end, a second, narrower, width in a downstream portion ending at said downstream end, and a tapered portion connecting said upstream portion to said downstream portion;
   a first inlet passing through said plate and forming a first inlet junction with said upstream end of said channel;
   an outlet passing through said plate and forming an outlet junction with said downstream end of said channel;
   a second inlet passing through said plate and forming a second inlet junction with said channel, narrower than said first inlet junction, between said first inlet junction and said outlet junction, and wherein said second inlet is in said upstream portion or said tapered portion of said flow channel; and a plurality of additional inlets passing through said first plate and forming a plurality of junctions with said channel between said second inlet and said outlet.

30. A sheath flow module, comprising:

a plate having formed therein:

a laminar flow channel formed in a first surface of said plate, said flow channel comprising an upstream end and a downstream end;

a first inlet passing through said plate and forming a first inlet junction with said upstream end of said channel;

an outlet passing through said plate and forming an outlet junction with said downstream end of said channel;

a second inlet passing through said plate and forming a second inlet junction with said channel, narrower than said first inlet junction, between said first inlet junction and said outlet junction; and wherein the depth of said channel increases at said second inlet junction.

31. The sheath flow module of claim 30 wherein said flow channel has a first width in an upstream portion starting at said upstream end, a second, narrower, width in a downstream portion ending at said downstream end, and a tapered portion connecting said upstream portion to said downstream portion, and wherein said second inlet is in said upstream portion or said tapered portion of said channel.

32. A sheath flow module, comprising;

a plate having formed therein:

a laminar flow channel formed in a first surface of said plate, said flow channel comprising an upstream end and a downstream end;

a first inlet passing through said plate and forming a first inlet junction with said upstream end of said channel;

an outlet passing through said plate and forming an outlet junction with said downstream end of said channel;

a second inlet passing through said plate and forming a second inlet junction with said channel, narrower than said first inlet junction, between said first inlet junction and said outlet junction; and a third inlet passing through said plate and forming a third inlet junction with said channel between said second inlet and said outlet, said third inlet junction being wider than said second inlet junction; and wherein the depth of said channel increases at said second inlet junction and increases again at said third inlet junction.

33. The sheath flow module of claim 32 wherein said flow channel has a first width in an upstream portion starting at said upstream end, a second, narrower width in a downstream portion ending at said downstream end, and a tapered portion connecting said upstream portion to said downstream portion, and wherein said second and third inlets are in said upstream portion or said tapered portion of said channel.

34. The sheath flow module of claim 33 wherein the depth of said channel decreases in said tapered portion.

35. A method of surrounding a center fluid stream on at least two sides by a sheath fluid, comprising the steps of:

providing a sheath flow module, comprising:

a plate having formed therein:

a laminar flow channel formed in a first surface of said plate, said flow channel comprising an upstream end and a downstream end;

a first inlet gassing through said plate and forming a first inlet junction with said upstream end of said channel;

an outlet passing through said plate and forming an outlet junction with said downstream end of said channel; and a second inlet passing through said plate and forming a second inlet junction with said channel, narrower than said first inlet junction, between said first inlet junction and said outlet junction;

injecting a sheath fluid via said first inlet through said first inlet junction into said laminar flow channel; and injecting a sample fluid containing reporter beads as a center fluid into said laminar flow channel via said second inlet through said second inlet junction whereby said sheath fluid surrounds said center fluid on at least two sides thereof.

36. A method of surrounding a center fluid stream on at least two sides by a sheath fluid, comprising the steps of:

xproviding a sheath flow module, comprising:

a plate having formed therein:

a laminar flow channel formed in a first surface of said plate, said flow channel comprising an upstream end and a downstream end;

a first inlet passing through said plate and forming a first inlet junction with said upstream end of said channel;

an outlet passing through said plate and forming an outlet junction with said downstream end of said channel; and a second inlet passing, through said plate and forming a second inlet junction with said channel, narrower than said first inlet junction. between said first inlet junction and said outlet junction, injecting a sheath fluid, wherein said sheath fluid is a sample fluid, via said first inlet through said first inlet junction into said laminar flow channel; and injecting a center fluid containing reporter beads into said laminar flow channel via said second inlet through said second inlet junction whereby said sheath fluid surrounds said center fluid on at least two sides thereof.

37. The method of claim 36 wherein the densities of said sheath and center fluids are approximately equal and the density of said reporter beads is greater than the density of said fluids.

38. The method of claim 37 wherein said sample fluid contains a reagent.

39. The method of claim 37 wherein said module is oriented so that said inlets are above said channel.

40. The method of claim 39 wherein said module is oriented so that said downstream end is lower than said upstream end.

41. The method of claim 36 wherein the densities of said sheath and center fluids and said reporter beads are approximately equal.

42. A sheath flow module, comprising:

a plate having formed therein:

a laminar flow channel formed in a first surface of said plate, said flow channel comprising an upstream end and a downstream end wherein said flow channel has a first width in an upstream portion starting at said upstream end, a second, narrower, width in a downstream portion ending at said downstream end, and a tapered portion connecting said upstream portion to said downstream portion;

a first inlet passing through said plate and forming a first inlet junction with said upstream end of said channel;

an outlet passing through said plate and forming an outlet junction with said downstream end of said channel;

a second inlet passing through said plate and forming a second inlet junction with said channel, narrower than said first inlet junction, between said first inlet junction and said outlet junction and wherein said second inlet is in said upstream portion or said tapered portion of said channel; and further comprising in said downstream portion of said channel, a measurement zone.

43. A sheath flow module comprising, a plate having formed therein:

a laminar flow channel formed in a first surface of said plate, said flow channel comprising an upstream end and a downstream end wherein said flow channel has a first width in an upstream portion starting at said upstream end, a second, narrower, width in a downstream portion ending at said downstream end, and a tapered portion connecting said upstream portion to said downstream portion;

a first inlet passing through said plate and forming a first inlet junction with said upstream end of said channel;

an outlet passing through said plate and forming an outlet junction with said downstream end of said channel;

a second inlet passing through said plate and forming a second inlet junction with said channel, narrower than said first inlet junction, between said first inlet junction and said outlet junction; and a third inlet passing through said plate and forming a third inlet junction with said channel between said second inlet and said outlet, said third inlet junction being wider than said second inlet junction;

wherein the depth of said channel increases at said second inlet junction and increases again at said third inlet junction;

wherein said second and third inlets are in said upstream portion or said tapered portion of said channel; and further comprising in said downstream portion of said channel, a measurement zone.

44. A method of surrounding a center fluid with a sheath fluid, comprising the steps of:

providing the sheath flow module of claim 43;

injecting a first sheath fluid via said first inlet through said first inlet junction into said laminar flow channel and a second sheath fluid via said third inlet through said third inlet junction into said laminar flow channel;

injecting a center fluid into said laminar flow channel via said second inlet through said second inlet junction, whereby said sheath fluid surrounds said center fluid;

wherein at least one of said center fluid or said first or second sheath fluids contain particles; and whereby said particles are hydrodynamically focused in said narrower width of said downstream portion of said laminar flow channel so that they flow through said measurement zone in a single file manner.

45. A sheath flow module, comprising:

a plate having formed therein:

a laminar flow channel formed in a first surface of said plate, said flow channel comprising an upstream end and a downstream end;

a first inlet passing through said plate and forming a first inlet junction with said upstream end of said channel;

a second inlet passing through said plate and forming a second inlet junction with said channel, narrower than said first inlet junction, between said first inlet junction and said downstream end; and two or more branching flow channels joining said laminar flow channel at said downstream end.

46. A sheath flow module, comprising:

a plate having formed therein:

a laminar flow channel formed in a first surface of said plate, said flow channel comprising an upstream end and a downstream end;

a first inlet passing through said plate and forming a first inlet junction with said upstream end of said channel;

a second inlet passing through said plate and forming a second inlet junction with said channel, narrower than said first inlet junction, between said first inlet junction and said downstream end;

wherein said laminar flow channel does not decrease in depth downstream from said second inlet junction;

a first fluid flowing through said first inlet and a second fluid flowing through said second inlet such that said first fluid is in laminar flow with said second flow, said sheath flow module being constructed and arranged such that said second fluid is surrounded on at least two sides by said first fluid; and said plate having a downstream edge through which said flow channel exits at said downstream end of said flow channel.

47. A method for creating a flame with an inner core, surrounded by an outer sheath of flame using the sheath flow module of claim 46, comprising the steps of:

introducing into said laminar flow channel a combustible sheath fluid via said first inlet through said first inlet junction;

introducing into said laminar flow channel a combustible center fluid via said second inlet through said second inlet junction, whereby said sheath fluid surrounds said center fluid; and combusting said fluids to form said flame at the downstream end of said laminar flow channel.

48. A method of obtaining an emission spectrum of a particle using a sheath flow module comprising:

a plate having formed therein:

a laminar flow channel formed in a first surface of said plate, said flow channel comprising an upstream end and a downstream end;

a first inlet passing through said plate and forming a first inlet junction with said upstream end of said channel;

a second inlet passing through said plate and forming a second inlet junction with said channel, narrower than said first inlet junction, between said first inlet junction and said downstream end;

said plate having a downstream edge through which said flow channel exits at said downstream end of said flow channel;

said method comprising the steps of:

injecting into said laminar flow channel a flammable fluid via said first inlet;

injecting said particle into said laminar flow channel via said second inlet;

igniting said flammable fluid at said downstream edge of said plate; and monitoring said emission spectrum of said particle.

\* \* \* \* \*

UNITED STATES PATENT AND TRADEMARK OFFICE
CERTIFICATE OF CORRECTION

PATENT NO.    : 6,159,739
DATED         : December 12, 2000
INVENTOR(S)   : Weigl et al.

Page 1 of 1

It is certified that error appears in the above-identified patent and that said Letters Patent is hereby corrected as shown below:

Column 12,
Line 6, please delete "(86)" and replace with -- (8*b*) --.

Column 18, claim 22,
Line 30, please delete "18" and replace with -- 21 --.

Column 19, claim 35,
Line 62, please delete "gassing" and replace with -- passing --.

Column 20, claim 36,
Line 14, please delete "xproviding" and replace with -- providing --.

Signed and Sealed this

Twenty-sixth Day of March, 2002

Attest:

*Attesting Officer*

JAMES E. ROGAN
*Director of the United States Patent and Trademark Office*